United States Patent [19]

Schurman

[11] 4,383,523
[45] May 17, 1983

[54] CERVICAL BRACE

[76] Inventor: John R. Schurman, 7326 Cascade Woods Dr., SE., Grand Rapids, Mich. 49506

[21] Appl. No.: 159,047

[22] Filed: Jun. 13, 1980

[51] Int. Cl.³ .............................................. A61H 1/02
[52] U.S. Cl. ...................................... 128/75; 128/78; 128/87 B; 128/DIG. 23
[58] Field of Search ...................... 128/69, 75, 76, 78, 128/84 R, 84 C, 87 B, DIG. 23

[56] References Cited

U.S. PATENT DOCUMENTS

| | | | |
|---|---|---|---|
| 1,301,276 | 4/1919 | Kroetz | 128/DIG. 23 |
| 2,009,011 | 7/1935 | Gribbon | 128/577 |
| 2,223,276 | 11/1940 | Ward | 128/DIG. 23 |
| 2,820,455 | 1/1958 | Hall | 128/DIG. 23 |
| 3,177,869 | 4/1965 | Bartels | 128/DIG. 23 |
| 3,667,457 | 6/1972 | Zumaglini | 128/75 |
| 3,724,452 | 4/1973 | Mitschke | 128/DIG. 23 |
| 4,120,297 | 10/1978 | Rabischong | 128/78 |

OTHER PUBLICATIONS

Aluminum Finger Splint Strips; Richard's Fracture and Orthopaedic Supplies; 5/1966.
Orthopedic Corsets and Belts; Orthopedic Appliance Atlas; ©1952.

Primary Examiner—Richard J. Apley
Assistant Examiner—David J. Brown
Attorney, Agent, or Firm—Waters, Lesniak & Willey

[57] ABSTRACT

A cervical brace comprises independently adjustable chin support and occipital supports for constraining movement of the head in any direction. The chin support comprises a chin rest pivotably mounted on a front support mechanism that includes a stationary base member and a vertically adjustable front support member mounted on the front base member. The occipital support comprises an occipital rest for engaging the lower rear portion of the head and a rear support mechanism that includes a vertically movable rear support member mounted on a rear base member, with the rear base member including a pelvic support flange that rests on the pelvis of the patient so as to support the brace from the pelvis instead of the shoulders of the patient. The chin and occipital rests are connected together by means of rigid lateral slide supports, the length of which can be adjusted to move the chin and occipital rests closer together or further apart. The front and rear support mechanisms are held in position on the body by means of a fabric corset. In an alternative embodiment, the supports are mounted on a rigid thermoplastic vest of the type of vest used for a halo brace.

12 Claims, 9 Drawing Figures

CERVICAL BRACE

BACKGROUND OF THE INVENTION

1. Field of the Invention

This invention relates to a cervical brace and more particularly to a cervical brace for maximum patient support wherein the patient's head is held rigidly in place by widely adjustable chin and occipital supports that are strapped to the torso of the patient and supported from the pelvis of the patient instead of the shoulders.

2. Description of Prior Art

An injury or deficiency in the spinal column frequently requires that the patient be placed for a substantial period of time in a restraining brace. Different braces are designed for different problems and different areas of the spinal column.

The three principal areas of the spinal column are the lumbar area or lower back; the dorsal area or middle back, and the cervical area or upper spine or neck.

One type of brace used for cervical support is a so-called "halo" brace. With this type of apparatus a halo or ring is rigidly attached to the skull of the patient and the halo is held rigidly in place by a support mechanism that is attached to the body of the patient. This type of support mechanism is employed where it is essential to hold the head rigidly in place. Obviously this type of brace involves severe discomfort to the patient since the halo is, in effect, bolted directly into the patient's skull.

Another type of cervical brace customarily used for less severe injuries is a so-called Forrester collar. With this type of apparatus a ring-like support member encircles the patient's neck and supports from underneath the chin areas and occipital (or lower rear) portions of the head. Leather straps may hold front and rear portions of this ring together so that the ring can be separated for installation of the collar and tightened on the person's neck. The ring is then supported by a collar that rides on the patient's shoulders.

The problem with a collar that rides on the patient's shoulders is that the patient's shoulders are not necessarily held in a fixed position with respect to the head. Thus, when the patient shrugs his shoulders or makes a similar shoulder movement, this movement is transmitted from the collar to the support mechanism and permits or actually causes movement of the head.

A Forrester collar also may be supplemented with a pelvic support that rides on the pelvis of the patient.

Typically braces that engage the chin and occipital portions of the head provide unsatisfactory adjustment capabilities for fitting the brace satisfactorily and rigidly to different patients. Some devices provide crude adjustment between the chin and occipital supports by means of a leather strap attaching the two together. Some braces also provide vertical adjustment of the head support members and some provide for some limited pivotal movement of the head support member as a unit. Such adjustment mechanisms are not entirely satisfactory and provide an incomplete fit for a wide variety of patients. This limits the amount of rigidity that can be accomplished with the brace and makes it necessary to use a brace such as a halo brace when extreme rigidity is required in the brace.

One of the important objects of the present invention is to provide a comfortable, well-fitting, and widely-adjustable cervical brace that supports the chin and occipital portions of the head with sufficient rigidity for even the most severe cervical injuries that would otherwise require a halo brace.

SUMMARY OF THE INVENTION

In accordance with the present invention, a cervical brace for supporting the cervical portion of a patient's spine comprises a chin support mechanism for engaging and supporting the patient's chin so as to prevent downward or sidewards movement of the chin and head. The position of the chin support mechanism is vertically adjustable and horizontally and pivotally adjustable in a forward and backward direction. An occipital support mechanism engages and supports the occipital or lower rear portion of the patient's head so as to prevent backward or sidewards movement of the head, with the position of the occipital support mechanism being adjustable in a direction toward and away from the chin support mechanism and being adjustable in a vertical direction with respect to the patient. The position of the occipital support mechanism also is pivotally adjustable in a forward and backward direction independent of the pivotal position of the chin support mechanism. The independent adjustment features of the chin and occipital support mechanisms make it possible to fit the brace properly and snugly to the head of each individual patient. The chin and occipital support mechanisms are then lockable in their adjusted positions to hold the patient's head rigidly yet comfortably in place.

The chin support mechanism comprises a chin rest that fits under the patient's chin to constrain downward and sideward movement of the chin. The chin rest is pivotally mounted on a front support mechanism that is positioned adjacent the chest of the patient and extends upwardly to the chin rest. The front support mechanism is adjustable in an upward and downward direction.

The occipital support mechanism similarly comprises an occipital rest that engages and supports the occipital portion of the patient's head so as to constrain backwards and sideward movement of the head. The occipital rest is mounted on a rear support mechanism that rides on the pelvis of the patient and extends upwardly into engagement with the occipital rest. The occipital rest is pivotally mounted on the rear support mechanism, and the rear support mechanism is vertically adjustable to permit vertical adjustment of the occipital rest.

To reduce expense the front and rear supports are interchangeable and the supports and base members are formed out of flat stock in a stamping operation.

The occipital and chin rests are interconnected by rigid lateral support members on each side of the rests, with the length of each lateral support member being adjustable so as to move the chin and occipital rests toward or away from each other to fit a particular patient.

A torso attachment means, preferably in the form or a corset or rigid plastic vest, holds the front and rear support mechanisms in fixed positions on the torso of the patient.

The front and rear support mechanisms comprise base members that are held in a fixed position with respect to the torso of the patient and vertically movable support members mounted on the base members. The front and rear support members slide on the base members and are locked in a position on the base members by locking plates that fit over the support members and are attached to the base members by threaded or other axially movable fasteners.

The chin and occipital rests are pivotally mounted on the tops of the front and rear support members by means of threaded axles that extend outwardly from the sides of the support members. These axles fit through openings in flanges on the chin and occipital rests, and threaded nuts on the ends of the axles hold the rests in a desired position.

The components of the present invention are formed of a radio luscent material (i.e., material that is invisible to X-rays). Magnesium-aluminum alloys are used for all metal components, with the pelvic support being formed of a relatively soft alloy that permits the pelvic support to be conformed to the shape of the patient's hips. Other components, notably the metal portion of the chin support, are formed of harder, more rigid alloys of magnesium and aluminum.

The present invention is designed primarily for providing a maximum support for cervical injuries, but it also can be used for lesser injuries and for providing support for the dorsal area of the spine from the D7 vertebra and above.

These and other features of the present invention are described below and shown in the appended drawings.

BRIEF DESCRIPTION OF THE DRAWINGS

FIG. 3 is a front elevational view of the front support mechanism of the present invention.

FIG. 4 is a rear elevational view of the rear support mechanism of the present invention.

DETAILED DESCRIPTION OF THE PREFERRED EMBODIMENTS

Figure 1:
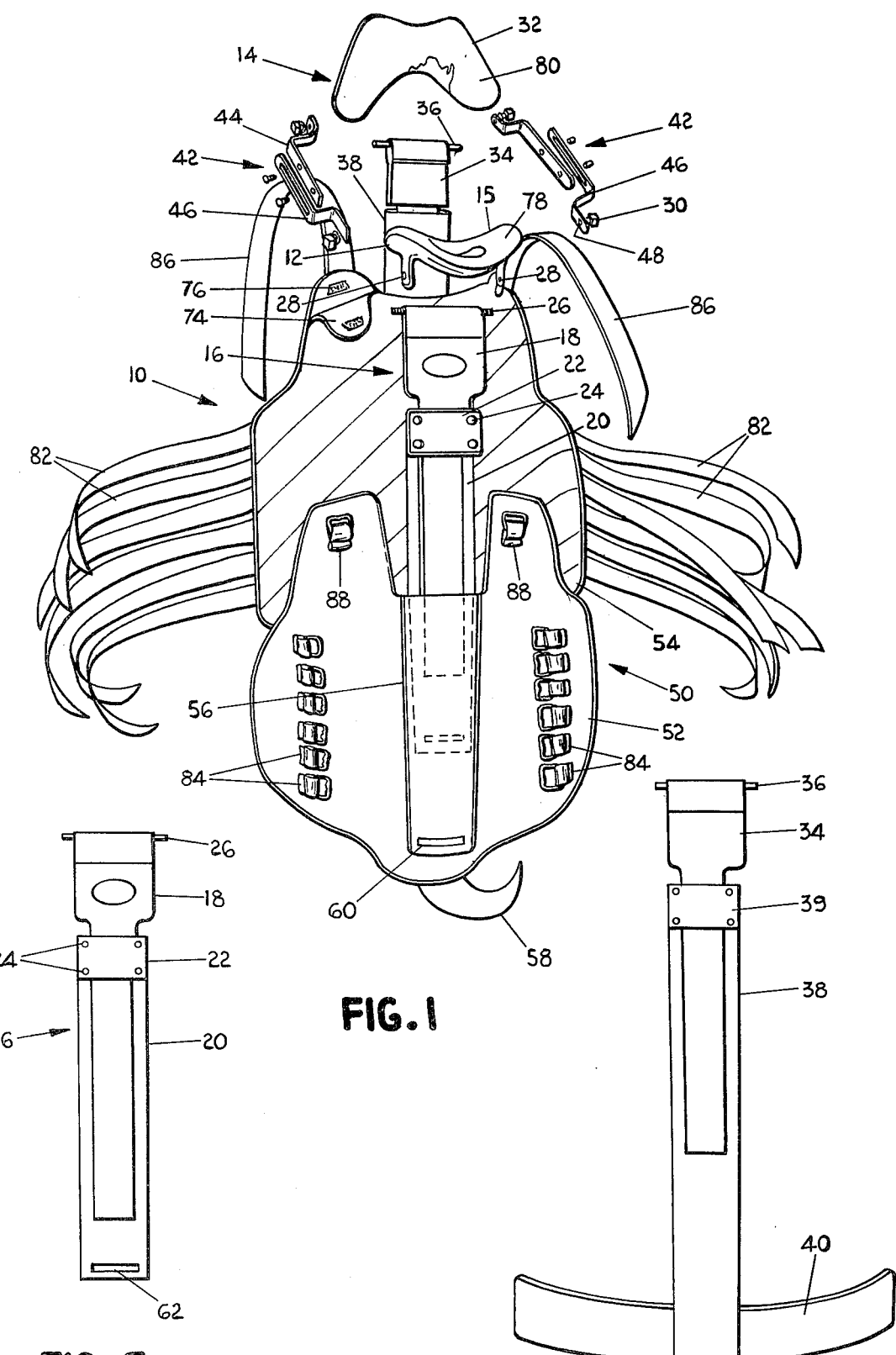
FIG. 1 is a perspective, exploded view of the cervical brace of the present invention.
Figure 2:
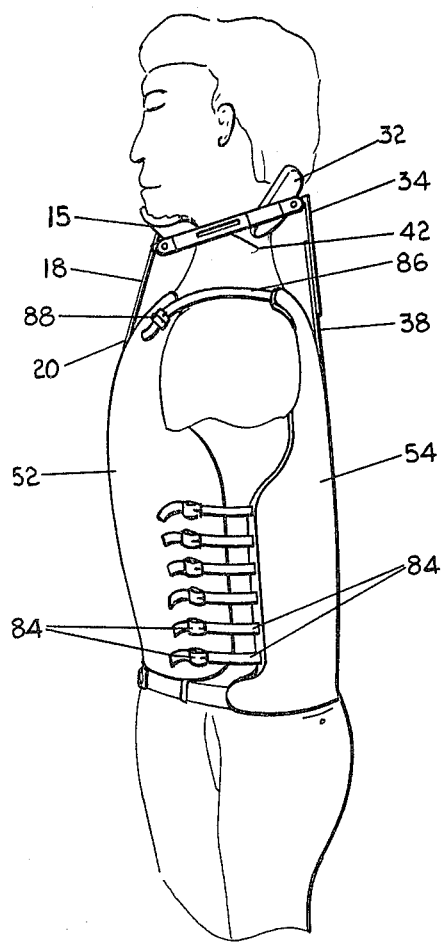
FIG. 2 is a side view showing the brace in position on a patient.
Figure 5:
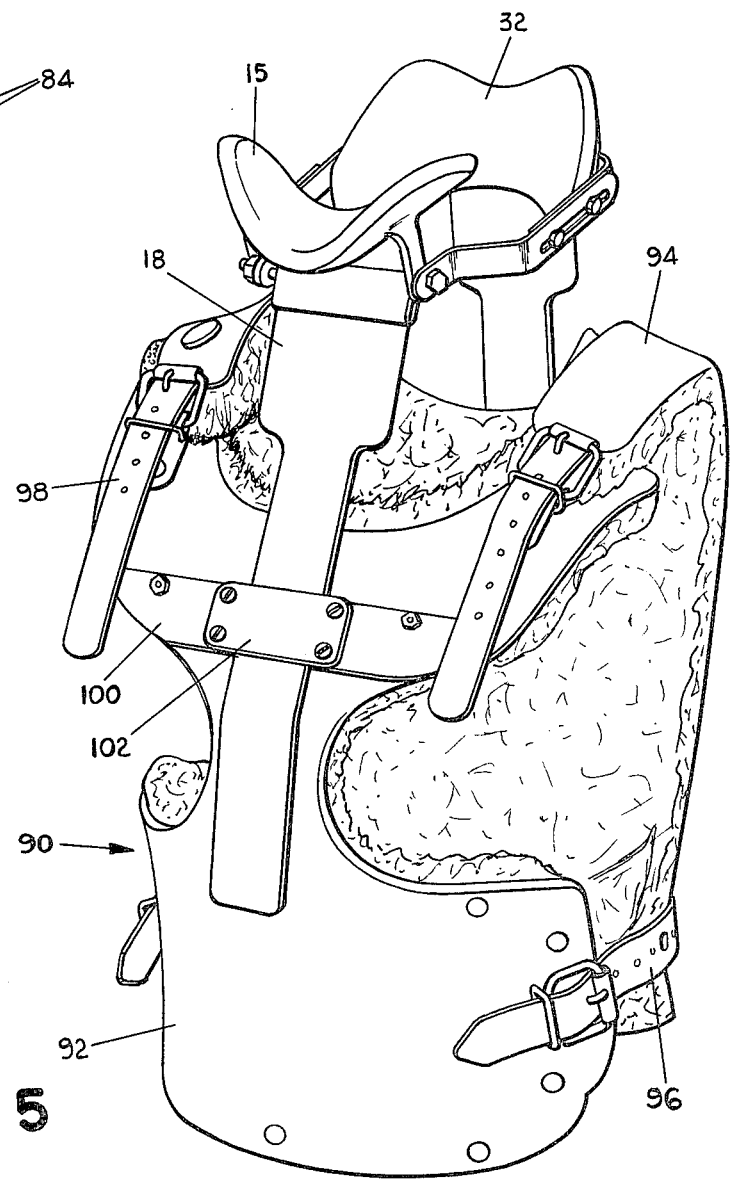
FIG. 5 is a perspective view showing an adaptation of the present invention employed for affixing the support mechanism to a hard plastic vest of the type used for a halo brace.

Referring now to the drawings, cervical brace 10 comprises a chin support mechanism 12 for engaging and supporting the patient's chin and an occipital support mechanism 14 for engaging and supporting the occipital portion or lower rear portion of the patient's head. The chin and occipital support mechanisms operate together to hold the patient's head rigidly in place and prevent movement of the head in any direction.

Chin support mechanism 12 comprises a chin rest 15, which is pivotally mounted on a front support mechanism 16. Front support mechanism 16 includes a support member 18 slideably mounted on a base member 20. A locking plate 22 fits over the flat support member 18 and is attached to the base member by means of threaded fasteners 24 or other axially movable fasteners. The fasteners are threaded into the base member such that when the fasteners are tightened, the locking plate clamps down on the support member and holds it in any desired position. The fasteners similarly can be loosened to permit vertical adjustment of the support member to any desired position.

The chin rest is pivotally attached to the upper end of the support member by means of a threaded axle 26 that extends outwardly from each side of the support member. The ends of the threaded axle fit through openings in spaced flanges 28 on the underside of the chin rest. Lock nuts 30 and washers fit on the threaded axles and are tightened to hold the chin rest in any desired position.

The occipital support mechanism is similar to the chin support mechanism and includes an occipital rest 32 shaped to engage the occipital portion of the head and prevent sideways or backward movement of the head. Occipital rest 32 is attached to a rear support member 34 by means of threaded axle 36 at the upper end of the support member. Rear support member 34 is identical to front support member 18, and the two support members are interchangeable.

Rear support member 34 is slideably mounted on a rear base member 38 by means of a locking plate 39 of substantially the same design as locking plate 22. Rear base member 38 extends downwardly to a pelvic support member or flange 40 extending outwardly from the bottom of the base member. Pelvic support member 40 fits over and engages the pelvis of the patient such that the cervical brace is supported by the pelvis of the patient instead of by the shoulders of the patient (as with previous collars). The pelvis is relatively stationary and provides more rigid support for the collar than the patient's shoulders would provide.

The occipital and chin rests are interconnected by means of a pair of rigid lateral support members 42 on each side of the chin and occipital rests. Each lateral support member 42 comprises a pair of interconnected arms 44 and 46. One arm 46 has an elongated slot therein, and a pair of threaded fasteners fit through the slot and screw into threaded openings in the other arm 44. When the fasteners are loosened, the length of the lateral support member can be adjusted by moving the arms relative to each other. This causes the chin and occipital rests to be moved toward or away from each other. When the proper fit is obtained, the threaded fasteners are tightened and the lateral support is locked in a fixed position.

The lateral support member is pivotally attached to the chin and occipital rests by means of threaded axles 26 and 36, which fit through openings 48 in the ends of the arms. Lock nuts 30 hold the lateral support members in place.

The front and rear support mechanisms are held in a rigid position against the torso of the patient by means of a fabric corset 50 that includes a front section 52 and a rear section 54. Front section 52 includes a central downwardly extending pocket 56 into which the front support mechanism fits. A strap 58 fits through a slotted opening 60 in the lower end of the pocket and through a slot 62 in the lower end of base member 20 to hold the base member firmly in position in the pocket.

The rear base member 38 with the outwardly extending pelvic support 40 fits upwardly through a central pocket 64 in the rear section of the corset, with a lateral extending portion 66 at the lower end accommodating pelvic support 40. An opening 70 at the bottom of the rear portion of the corset permits the rear support mechanism to be fitted through the corset in an upward direction. A Velcro-type fastener 72 closes the opening after the rear support mechanism has been inserted.

Because of the fact that the corset is in contact with the body of the patient and therefore periodically requires washing, a removable liner 74 formed of washable cloth or the like is attached to the inside surface of the corset. The liner can be attached to the corset by means of Velcro-type fasteners 76 or the like. To remove the liner, the corset need only be loosened so that the liner can then be installed and the corset tightened again. Similar liners 78 and 80 are provided for the interior surfaces of the chin rest and occipital rest.

The front and rear portions of the corset are securely fastened together by a plurality of straps 82 extending outwardly from the sides of the rear portion of the corset that engage buckles 84 on the sides of the front portion of the corset.

A pair of straps 86 extend upwardly from the top of the rear portion of the corset over the shoulders of the patient and are fastened in place by buckles 88 at the top of the front portion of the corset. These straps do not serve as a shoulder support for the brace but merely serve as an additional means for holding the corset firmly in place on the patient's torso.

When the cervical brace of the present invention is used by a person who has previously been fitted with a halo brace, it is possible to employ some of the apparatus used for the halo brace. A thermoplastic vest 90 is used with a halo brace to hold the halo in a fixed position on the torso of the patient. This vest comprises a fleece-lined plastic shell having a front section 92 and rear section 94 attached together by side straps 96 and shoulder straps 98. To employ this vest with the cervical brace of the present invention, the front base member is a plate 100 mounted on the front section of the best. A locking plate 102 holds front support member 18 in place. Front support member 18 is the same as used for the corset supported brace.

Figure 6:
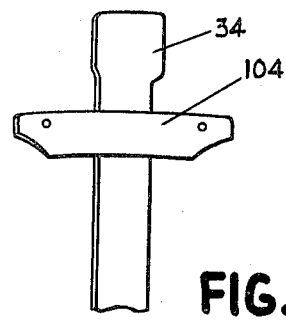
FIG. 6 is a front elevational view of the front support mechanism of the embodiment shown in FIG. 5.
Figure 7:
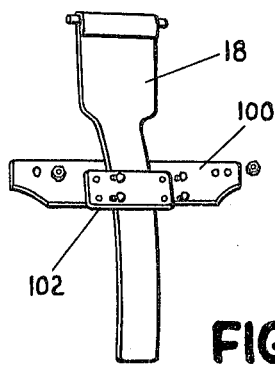
FIG. 7 is a front elevational view of the rear support mechanism of the embodiment shown in FIG. 5.
Figure 8:
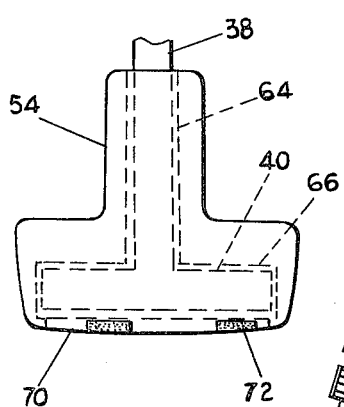
FIG. 8 is a fragmentary view showing the lower portion of the rear support mechanism of the FIG. 1 embodiment encased in the rear portion of the corset.

The base member for the rear support member 34 (the same as the one used for the corset supported brace) is a mounting plate 104 (see FIG. 6) which is attached to the rear portion of the vest. A locking plate substantially the same as locking plate 102 holds the rear support member to the rear mounting plate.

The remaining portions of the cervical brace used in connection with the halo vest are the same as described previously.

Figure 9:
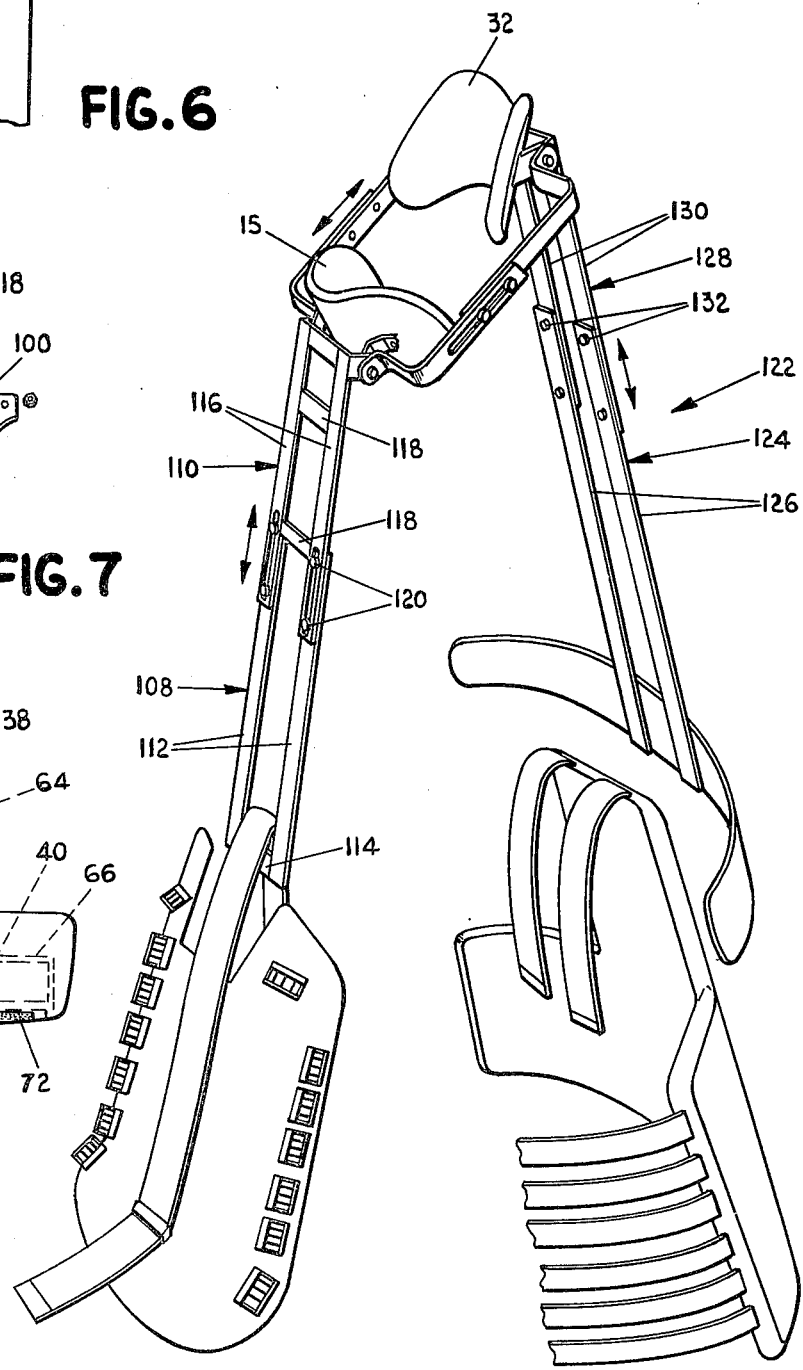
FIG. 9 is a perspective view of a second embodiment of the cervical brace of the present invention.

While the foregoing construction of the present invention is preferred, another embodiment of the present invention is shown in FIG. 9. In this embodiment, the principal difference is the construction of the front and rear support mechanisms. Front support mechanism 106 comprises a pair of adjustably interconnected frame members, a lower frame member 108 and an upper frame member 110. Lower frame member 108 comprises a pair of parallel rails 112 interconnected by a cross member 114. Upper frame member 110 similarly includes a pair of parallel rails 116 interconnected by cross members 118. Upper rails 116 are provided with slotted openings along the lower ends thereof and threaded fasteners 120 fit through the slotted openings into threaded openings in lower rails 112. The length of the front support member can be adjusted by loosening fasteners 120 sliding the upper frame upwardly or downwardly over the lower frame and then retightening the threaded fasteners.

The rear support mechanism 122 is constructed in the same fashion, with the support member including a lower support member 124 formed of parallel rails 126 and and upper support member 128 formed of parallel support rails 130. Threaded fasteners 132 extending through slotted openings in rails 130 and into threaded openings in rails 126 provide for vertical adjustment of the rear support mechanism.

The remaining structure of the FIG. 9 embodiment is substantially the same as the embodiment described above and provides the same independent pivotal movement of the chin and occipital support members and adjustable rigid interconnection of the occipital and chin rests.

The components of the present invention are all formed of radio luscent materials. The metal components are formed of magnesium-aluminum alloys, the pelvic support being formed of a relatively soft alloy to permit the pelvic support to be conformed to the hips of the patient. Other components, notably the chin support, are formed of harder, more rigid magnesium-aluminum alloys.

To reduce expense and provide component interchangeability, the front and rear support members are interchangeable, and the support members and base members are formed out of flat stock in a stamping operation.

It should be understood that the foregoing embodiments are merely exemplary of the preferred practice of the present invention and that various changes and modifications may be made in the arrangements and details of construction of the embodiments shown and described herein without departing from the spirit and scope of the present invention.

The embodiments of the invention in which an exclusive property or privilege is claimed are defined as follows:

1. A cervical brace for supporting the cervical portions of a patient's spine comprising:

chin support means for engaging and supporting the patient's chin so as to prevent downward or sideward movement of the chin and head, the position of the chin support means being vertically and horizontally adjustable and pivotally adjustable in a forward and backward direction, the chin support means comprising:

a chin rest shaped to engage the underside of a patient's chin so as to constrain downward and sideward movement of the chin; and a front support mechanism positioned adjacent the chest of the patient and extending upwardly to the chin rest, the chin rest being mounted on the front support mechanism for pivotally adjustable movement in a forward and backward direction with respect to the front support mechanism, the front support mechanism being upwardly and downwardly adjustable to raise and lower the chin rest;

occipital support means for engaging and supporting the occipital portion of the patient's head so as to prevent backward or sidewards movement of the head, the position of the occipital support means being adjustable in a direction toward and away from the chin support means and being adjustable in a vertical direction with respect to the patient, the position of the occipital support means also being pivotally adjustable in a forward and backward direction independent of the pivoted position of the chin support means, the independent adjustment features of the chin and occipital support means permitting free and separate adjustment of the chin and occipital support means to fit the brace properly and snugly to the head of each individual patient, the chin and occipital support means then being lockable in their adjusted positions to hold the patient's head rigidly yet comfortably in place, the occipital support means comprising:

an occipital rest shaped to engage the occipital portion of the patient's head so as to constrain backward and sidewards movement of the head; and a rear support mechanism positioned adjacent the back of the patient and extending upwardly from a lower end, which comprises a pelvic support that rests on the pelvis of the patient, to an upper end, which supports the occipital rest, the occipital rest being mounted on the rear support mechanism for pivotally adjustable movement in a forward and backward direction with respect to the rear support mechanism, the rear support mechanism supporting the occipital rest from the pelvis and being upwardly and downwardly adjustable to raise and lower the occipital rest;

rigid lateral support members interconnecting the chin and occipital support means on each side of the patient's head, the length of each support member being selectively adjustable to move the chin and occipital support means toward or away from each other to fit the patient, the lateral support members being lockable at a desired length to rigidly maintain the desired separation between the chin and occipital support means; and torso attachment means for holding the front and rear support mechanisms in fixed positions on the torso of the patient.

2. A cervical brace according to claim 1 wherein:

the chin and occipital rests are mounted on the front and rear support mechanisms for adjustable pivotal movement in a vertical plane extending in a forward and backward direction with respect to the patient; and each lateral support member comprises a pair of elongated arms releasably fastened together such that the arms can be extended or retracted when released but are held rigidly together when fastened, the chin and occipital rests being attached to opposite ends of the interconnected arms, the lateral support members being pivotally connected to the chin and occipital rests such that the chin and occipital rests can be pivotally adjusted and the lateral support members can pivot with respect to the support mechanisms as the relative vertical positions of the chin and occipital rests are adjusted.

3. A cervical brace according to claim 1 wherein the front and rear supports comprise front and rear base members that are held in a fixed position with respect to the body of the patient and front and rear support members that are mounted on the base members for adjustable vertical movement with respect to the base members, the support members extending upwardly from the base members and being pivotally attached to the chin and occipital rests at upper ends thereof.

4. A cervical brace according to claim 3 wherein the base and support members are flat and ride on one another, each support member being held to each base member by a locking plate that fits over the support member and is fastened to the base member by axially tightenable fasteners such that tightening the fasteners locks the support member in place on the base member.

5. A cervical brace according to claim 3 wherein the torso attachment means comprises a corset that is strapped to the body of the patient, the corset having a rear section that retains the rear base member in position and a front section that retains the front base member in position, the front and rear sections of the corset being strapable together tightly on the patient so as to hold the base members in position, the base members being selectively removable from the corset.

6. A cervical brace according to claim 5 wherein the corset has a removable liner that contacts the body of the patient, the liner being releasably fastened to the corset, such that the liner can be removed periodically for cleaning.

7. A cervical brace according to claim 6 wherein the liner is held in place by interlocking fabric fasteners, and the chin and occipital rests are similarly provided with liners that are attached by interlocking fabric fasteners.

8. A cervical brace according to claim 1 wherein the chin and occipital support means are formed of radio luscent materials, with the front and back support mechanisms comprising metal members formed of magnesium-aluminum alloys.

9. A cervical brace according to claim 2 wherein the chin and occipital rests are mounted on the front and rear support mechanisms by bolts that extend through the respective rests and support mechanisms, and the rigid lateral support members are attached to the chin and occipital support means by the same bolts, with one lateral support being mounted on each side of the rests.

10. A cervical brace for supporting the cervical portions of a patient's spine comprising:

chin support means for engaging and supporting the patient's chin so as to prevent downward or sideward movement of the chin and head, the position of the chin support means being vertically and horizontally adjustable and pivotally in a forward and backward direction, the chin support means comprising a chin rest mounted for pivotal adjustment on a front support member, the front support member being mounted for vertical position adjustment on a front base member;

occipital support means for engaging and supporting the occipital portion of the patient's head so as to prevent backward or sidewards movement of the head, the position of the occipital support means being adjustable in a direction toward and away from the chin support means and being adjustable in a vertical direction with respect to the patient, the position of the occipital support means also being pivotally adjustable in a forward and backward direction independent of the pivoted position of the chin support means, the independent adjustment features of the chin and occipital support means permitting free and separate adjustment of the chin and occipital support means to fit the brace properly and snugly to the head of each individual patient, the chin and occipital support means then being lockable in their adjusted positions to hold the patient's head rigidly yet comfortably in place, the occipital support means comprising an occipital rest mounted for pivotal adjustment on a rear support member, the rear support member being mounted for vertical position adjustment on a rear base member;

rigid lateral support members interconnecting the chin and occipital support means on each side of the patient's head, the length of each support member being selectively adjustable to move the chin and occipital support means toward or away from each other to fit the patient, the lateral support members being lockable at a desired length to rigidly maintain the desired separation between the chin and occipital support means, the lateral support members being connected to non-pivoting portions of the chin and occipital support means, such that movement associated with pivotal adjustment of the chin or occipital support means is not translated to the other support means by the lateral support members; and torso attachment means for holding the front and rear base members in a fixed position with respect to the body of the patient.

11. A cervical brace according to claim 10 wherein the torso attachment comprises a removable fabric corset that is strapped to the patient's body and holds the base members in a fixed position on the body.

12. A cervical brace according to claim 10 wherein the torso attachment means comprises a solid thermoplastic vest, with the base members comprising mounting plates attached to the surface of the vest, the support members being attached to the mounting plates for adjustable vertical movement with respect to the mounting plates.

* * * * *